United States Patent [19]

Ambrus

[11] Patent Number: 5,051,264

[45] Date of Patent: Sep. 24, 1991

[54] POTENTIATION OF THE THROMBOLYTIC EFFECT OF PROUROKINASE TYPE PLASMINOGEN ACTIVATORS BY STREPTOKINASE

[75] Inventor: Clara M. Ambrus, Buffalo, N.Y.

[73] Assignee: Collaborative Research, Inc., Bedford, Mass.

[21] Appl. No.: 266,120

[22] Filed: Nov. 2, 1988

[51] Int. Cl.[5] .................. A61K 37/54; A61K 37/547; C12N 9/50; C12N 9/70
[52] U.S. Cl. .............................. 424/94.2; 424/94.63; 424/94.64; 435/215; 435/216; 435/219; 435/226
[58] Field of Search ................ 424/94.2, 94.64, 94.63; 435/219, 226, 215, 216

[56] References Cited

U.S. PATENT DOCUMENTS 4,178,368  12/1979  Heimburger et al. ............ 424/94.64

OTHER PUBLICATIONS

Verstraete et al., Blood, vol. 67, No. 6, (1986) pp. 1529–1541.

*Primary Examiner*—Jacqueline Stone
*Attorney, Agent, or Firm*—Wolf, Greenfield & Sacks

[57] ABSTRACT

The thrombolytic effect of known plasminogen activators such as tissue plasminogen activator (t-PA), prourokinase and modifications of t-PA and prourokinase is enhanced dramatically and unexpectedly when combined with streptokinase. The body is treated with a combination streptokinase and one or more plasminogen activators of the t-PA or prourokinase type to achieve an enhanced effect which has advantage in thrombolytic therapy including the treatment of myocardial infarction.

10 Claims, 2 Drawing Sheets

POTENTIATION OF THE THROMBOLYTIC EFFECT OF PROUROKINASE TYPE PLASMINOGEN ACTIVATORS BY STREPTOKINASE

BACKGROUND OF THE INVENTION

Control of the fibrinolytic system has been considered an important therapeutic goal because of the number of human disease states which could then be treated or prevented. For example, myocardial infarction, deep vein thrombosis, and pulmonary embolism all appear to involve undesirable fibrin clot formation. While many proteins interact in complex ways in fibrinolysis, some success in the treatment of myocardial infarction has been attained by use of various proteins termed plasminogen activators. It is known that the use of tissue plasminogen activators, prourokinase, urokinase itself and various second generation plasminogen activators derived from t-PA and prourokinase may be useful in the treatment of the body to obtain a thrombolytic effect in vivo.

As used in these specifications and claims, t-PA type plasminogen activator is meant to include and mean plasminogen activator of the tissue type known as (t-PA) as well as various derivatives thereof which plasminogen activator may occur naturally, or be derived by genetic engineering means. Similarly prourokinase type plasminogen activators are meant to include single chain prourokinase (scu-PA) itself and various second generation derivatives thereof having plasminogen activation properties as is known in the literature and will be described herein.

Such t-PA type or tissue type plasminogen activators are well known in the literature as are prourokinase type plasminogen activators as for example described in European Patent Application publication number 0,223,192 and referred to in said application.

It is pointed out in that application that t-PA is a well known tissue type plasminogen activator. Prourokinase is referred to therein as scu-PA and is a single chain form of urokinase type plasminogen activator.

The patent application suggests a synergistic effect when using t-PA in combination with prourokinase or urokinase type plasminogen activator. The synergistic effect obtained was found to be desirable in certain examples given.

Another known plasminogen activator of a wholly different type than t-PA and scu-PA is streptokinase. Streptokinase for some time had been the most widely used thrombolytic agent for myocardial infarction probably because it has been easier to obtain and far less expensive than tissue plasminogen activator type and prourokinase type plasminogen activators. Streptokinase is known as a nonenzyme protein produced by Lancefield group C strains of beta-hemolytic streptococci. It activates the fibrinolytic system indirectly by complexing with plasminogen to produce a modified plasminogen moiety. For purposes of this invention streptokinase activator as used herein is meant to include streptokinase itself as well as streptokinase plasminogen complexes.

SUMMARY OF THE INVENTION

It is an object of this invention to provide a treatment to the body by applyinq an advantaqeous combination of two different types of plasminogen activators one of which is streptokinase, in order to provide a therapy for thromboembolic disorders.

It is a further object of this invention to provide a combination of streptokinase and a prourokinase type plasminogen activator or tissue type plasminogen activator for use as an advantageous therapeutic pharmaceutical composition.

Still another object of this invention is to provide a method of treating the body using the pharmaceutical composition of the preceeding object.

Still another object of this invention is to provide a useful combination of plasminogen activators which can rapidly provide useful therapy in thromboembolic disorders with minimized hemorrhagic complications.

According to the invention a thrombolyticaly active pharmaceutical composition comprises a combination of streptokinase and a plasminogen activator selected from the group consisting of t-PA type plasminogen activators, pro-urokinase type plasminogen activators, and mixtures thereof. The combination material can be carried in a pharmaceutically acceptable excipient such as sterile saline.

According to the method of this invention, the body is treated to obtain a thromobolytic effect in vivo. A combination of streptokinase and plasminogen activator selected from the group consisting of t-PA type plasminogen activators and prourokinase type plasminogen activators and mixtures thereof is applied to the body. They can be applied as single combination in a pharmaceutically acceptable excipient or can be applied sequentially in reasonable periods of time so that the effect of the two are jointly applied to the body.

It is a feature of this invention that clots can be dissolved without substantial hemorrhagic complications. Clot dissolving can be carried out rapidly, efficiently, and substantially at the site of clot formation.

BRIEF DESCRIPTION OF THE DRAWINGS

The above and other feature objects and advantages of the invention will be better understood from the following description when read in conjunction with the following drawings in which.

DESCRIPTION OF PREFERRED EMBODIMENTS

According to the invention, streptokinase is applied to the body in conjunction with a tissue type plasminogen activator and/or prourokinase type plasminogen activator or combinations thereof to obtain a thrombolytic effect.

The streptokinase used can be any streptococci protein as is produced from Lancefield group C strains of beta hemolytic streptococci and which complexes with plasminogen. The mechanism of complexing has been published in several articles including J. Biol. Chem. 24, 6389, 1970; Biochem. Biophys.Acta 263, 610, 1974; Thromb.Diath.Hem. Suppl. 47, 37, 1971; ibid.21,594, 1969.

The streptokinase can be obtained from many manufacturers as for example, Hoechst Roussel of New Jersey under the trademark STREPTASE, from Kabi Vitrum AB of Stockholm, Sweden an Kabikinase. Kabikinase contains streptokinase which is a purified preparation of bacterial protein elaborated by group C B-Hemolytic streptococci. It is known as a white soluble white lyophilized powder for intravenous infusion. In the infusion form it can contain 11.0 mg sodium L-glutamate and 14.5 mg human albumin per 100,000 IU of streptokinase as stabilizers.

While the mechanism of this invention and the reason for the enhanced thrombolytic effect advantage by using streptokinase in connection with other plasminogen activators of this invention is not positively known, it is believed that a synergistic effect is obtained. Prourokinase type plasminogen activators believed to dissolve clots by being activated by small amounts of plasmin, which is spontaneously activated from plasminogen that has co-precipitated with fibrinogen. The active enzyme then activates the remaining plasminogen molecules and dissloves the clot. From older clots, plasminogen is partially leeched out and the process does not work. However, small amounts of streptokinase generates plasmin in the blood circulation, this absorbs to clots formed in the human body, which activates prourokinase, which in turn activates plasminogen to plasmin and dissolves clots without hemorrhagic complications.

Figure 1:
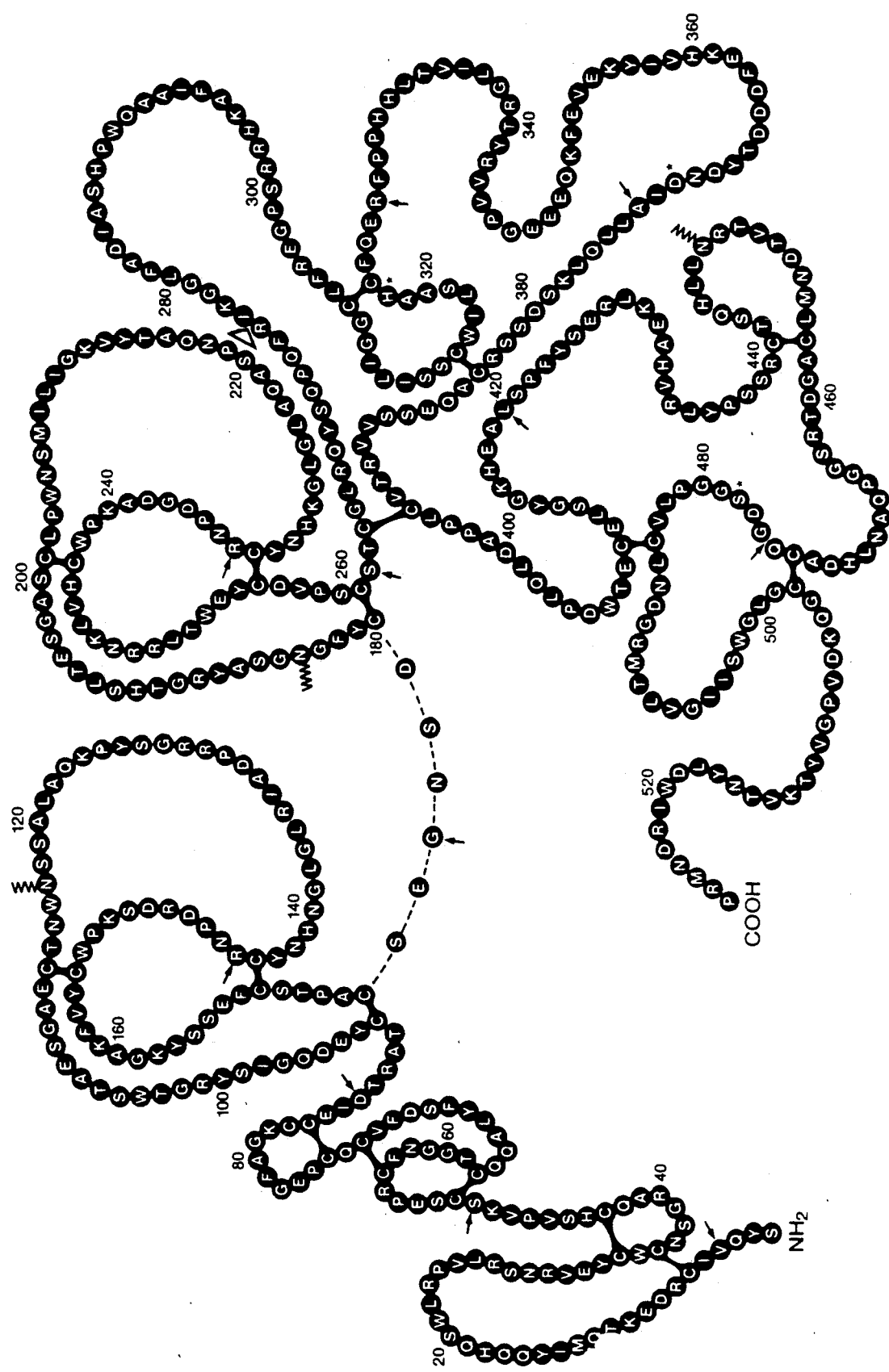
FIG. 1 is a schematic diagram of the structure of human tissue plasminogen activator.

Tissue type plasminogen type activators useful in this invention are known in the art and as described in European Patent Application 223,192 filed Nov. 11, 1986 and U.S. Pat. No. 4,752,603 and are illustrated in FIG. 1. Modifications of the amino acid sequence or second generation t-PA plasminogen activators can also be used.

Figure 2:
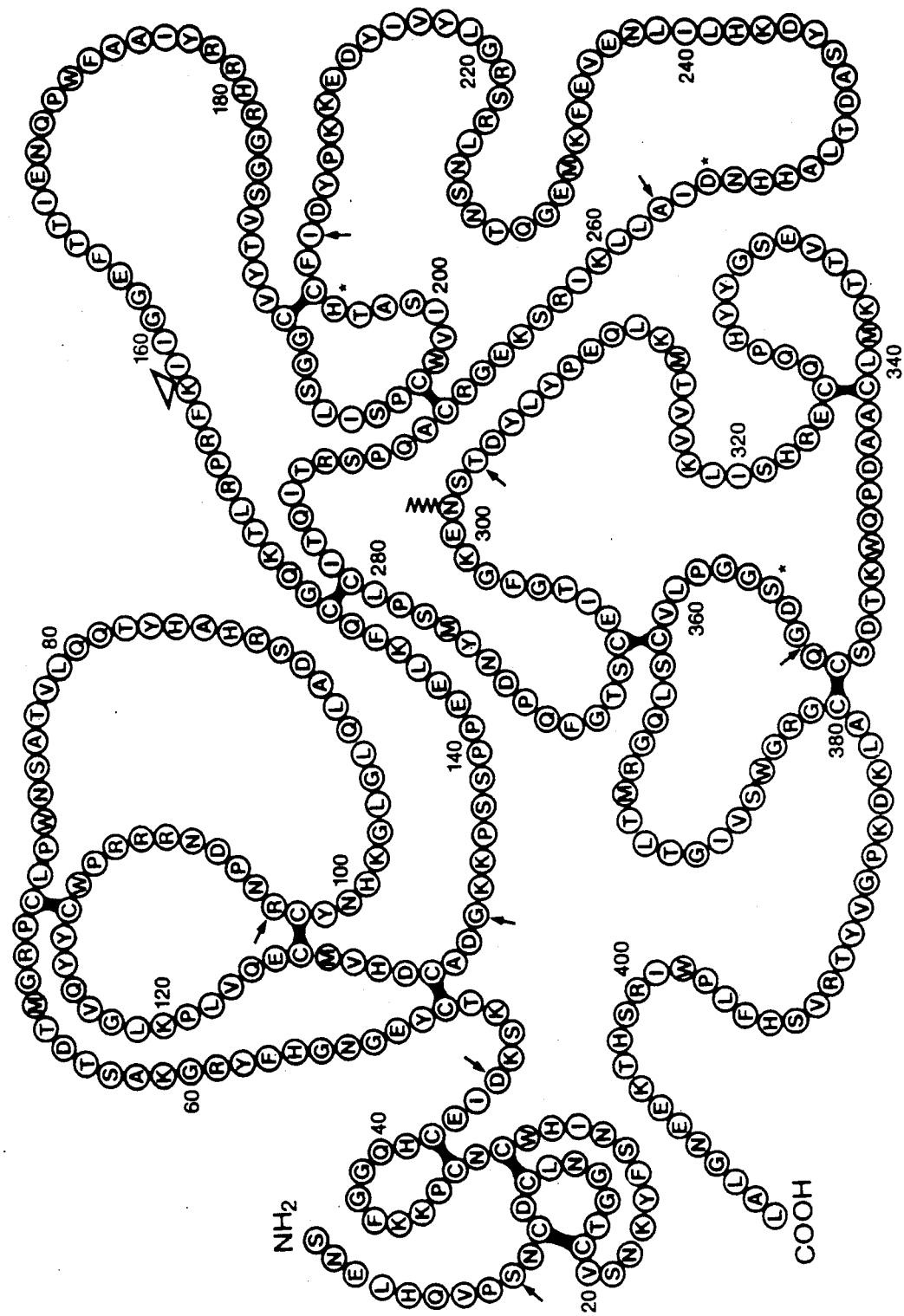
FIG. 2 is a schematic diagram of the structure of human prourokinase.

In FIGS. 1 and 2, the letter code for each amino acid is given in the open circles. The one letter abbreviations are those recommended by the IUPAC-IUB Commission on Biochemical Nomenclature. The cysteine residues are shaded. The solid black bars indicate the potential disulphide bridqes based on homology with other serine proteases. The arrows indicate the potential cleavage site between arginine and isoleucine which generates the two chain molecule from the one chain form. The zig-zag lines indicate potential glycosylations. The broken lines connect the six amino acids between the two kringles.

The prourokinase type plasminogen activators include prourokinase itself as shown in FIG. 2, as well as what is known as "second generation" prourokinase. These can be obtained directly from the body of humans or other animals althouqh human prourokinase is preferred. They can also be obtained by genetic engineering techniques as is known. A number of so called second generation plasminogen activators which are modifications of prourokinase are known and have been published in scientific journals and European Patent Applications. Listed below are certain of these second generation materials where amino acid residue numbering is according to u-PA-Holmes, W. E. et. al, 1985, Biotechnology 3; 923-929; t-PA-Pennica, D. et. al. 1983, Nature 301:214–221; Plasminogen-Forsgren, M., 1987 FEBS Lett. 213; 254–260. Abbreviations are PLG-K1=plasminogen Kringle 1; PLG-K4=plasminogen Kringle 4; uPA=urinary plasminogen activator; t-PA =tissue plasminogen activator:

1. Amino acid modified prourokinase compounds with increased physiological half life over prourokinase itself. Such compounds include substitutions at lys 158.. Such compounds are described in U.S. Pat. Application Ser. No. 07/012023 filed Feb. 19, 1987 which is incorporated by reference herein and European Patent Application 236,040 filed Feb. 19, 1987. Substitutions are described at lysine 158 where ala-158 glu-158 and met-158-ser-160 result. Additional second generation compounds are described in Genetech patent Application EP 200451 and Sagami European Patent Application 210,279.

2. In another group of prourokinase type plasminogen activators, non-glycosylated plasminogen activator is provided as described in U.S. Application 07/211,279 filed June 29, 1988 which is incorporated herein by reference. These applications describe prourokinase substituted at the ala 302, gln 302, val 304 and ala 304.

3. In still another group, shortened single chain plasminogen activators can be formed as described in U.S. Pat. Application 07/107,370 filed October 9, 1987 which is incorporated herein by reference and wherein the plasminogen activators are identified as N-gln150-scu-PA, N-arg154-scu-PA, N-arg156-scu-PA, N-phe157-scu-PA, N-lys 158-scu-PA.

4. Thrombin cut prourokinase as described in U.S. Pat. Application 07/143,975 filed Jan. 14, 1988 which is incorporated herein by reference can also be used as can plasminogen activators with increased fibrin selectivity comprising kringle fusions and the like as found in U.S. Pat. Application 07/170,751 filed Apr. 22, 1988 which is incorporated by reference. Such plasminogen activators along with plasminogen resistant prourokinase of the type covered by U.S. Pat. Application 07/233,212 filed Aug. 17, 1988, which is incorporated by reference herein, and identified as follows can be used.

scu-PA-pro1159
scu-PA-met1159
scu-PA-glu1159
scu-PA-asp1159
scu-PA-asn1159-ser16

Other second generation material as described in the following publications and patents may also be used.

A. de Vries,C.,Veerman, H., Blasi, F., & Pannekoek, H. 1988. Biochemistry 27: 2565–2572.
   tPA(1-262)-uPA (147-411)
   tPA(1-262)-uPA(134-411)

B. Sagami Chemical Research, patent application EP 231 883:
   tPA(1-3-G-51-265)-uPA (150-411)
   tPA(1-3-G-51-261)-uPA(132-411)
   tPA(174-265)-uPA(150-411)
   tPA(174-261)-uPA(132-411)
   tPA(207-265)-uPA(150-411)
   tPA(207-261)-uPA(132-411)

3. C. Nelles, L., Lijnen, H.R., Collen, D., & Holmes, W.E. 1987. J. Biol. Chem. 262: 10855-10862.
   tPA(1-263)-uPA(144-411)

D. Pierard, L., Jacobs, P., Gheyson, D., Hoylaerts. M., Andre, B., Topisirovic, L., Cravador, A., Foresta, F., Herzog, A., Collen, D., DeWilde, M., Bollen, A. 1987. J. Biol. Chem. 262: 11771-11778.
   tPA(1-67)-uPA(136-411)
   tPA(1-262)-uPA(139-411)
   tPA(1-313)-uPA(195-411)
   uPA(1-130)-tPA(173-262)-uPA(139-411)

E. Ehrlich, Bang, Little, Jaskunas, Weigel, Mattler & Harms. 1987. Fibrinolysis 1: 75-81. (Eli Lilly)
   t-PA deleted for both kringle 1 and kringle 2 domains
     t-PA deleted for finger, EGF, & kringle 1 domains F. Brown et al. 1988. J. Biol. Chem. 263: 1599-1602.
   t-PA deleted for EGF domain

G. Kalyan et al. 1988. J. Biol. Chem. 263: 3971-3978.
   t-PA deleted for finger & EGF domains H. Larsen, Henson & Blue. 1988. J. Biol. Chem. 263: 1023–1029.
t-PA deleted for finger &/or EGF domains
I. Lijnen, Nelles, Holmes & Collen. 1988. J. Biol. Chem. 263: 5594–5598.
N-leu144-scu-PA
J. Gheysen et al. 1987 J. Biol. Chem. 262: 11779–11784.
t-PA(1-67)-scu-PA(136-411) [t-PA finger domain fused to N-lys136-scu-PA]
K. Non-glycosylated t-PAs [see patent application of Genetech (EP 238304), Ciba-Geigy (EP 225286), Zymogentics (DE 3537176), & Chiron (EP 227462)] comprises alterations of asparagines 117, 184, & 448 to glutamine
L. Protease resistant t-PAs [see patent applications of Genentech (EP 199574), & Beecham (EP 233013)] comprises alteration of arg275 to a non-basic amino acid
II. Non-recombinant Methods—protein fusions utilizing one or both chains of the two-chain enzymes:
M. Nakayama, Y., Shinohara, M., Tani, T., Kawaguchi, T., Furuta, T., Izawa, T., Kaise, h., Miyazaki, W., & Nakano, Y. 1986. Thombosis & Haemostasis 56: 364–370.
PLG(77-560)-uPA(136-158; 159-411)
N. Robbins, K.C. and Tanaka, Y. 1986. Biochemistry 25: 3603–3611.
PLG(77-560)-uPA(159-411)
O. Beecham Group PLC. patent application EP 155 387:
PLG(77-560)-tPA(276-527)
tPA(1-275)-uPA(159-411)
PLG(77-560)-uPA(159-411)

Pharmaceutical compositions containing the novel combinations of plasminogen activators of this invention can have several forms so long as they are suitable for administration to man and animals. A form comprising intravenous infusion fluid or combination of infusion fluids is preferred since it is a commonly accepted method of administering streptokinase by itself and plasminogen activators by themselves to the body for advantageous thrombolytic effect. Such infusion fluids can combine mixtures of streptokinase with the other plasminogen activators of this invention. The activators can be separately packaged with an infusion fluid of streptokinase used at one time and an infusion fluid of the other plasminogen activator or combination thereof used at a second time, close in time to the first so that the combined effects can be felt on the body.

While specific dosages may vary greatly it is expected that in man, a dosage rate from about 1,000 to about 25,000 international units per Kg of body weight of streptokinase would be useful, proceeded by, followed by or simultaneously used with from about 0.05mg to about 1 mg/kg and preferably 0.1 mg to 0.5mg per kilogram of body weight of prourokinase type or tissue type plasminogen activator. More preferably the range of streptokinase used is from 2,000 to 12,500 international units per kilogram of body weight. The time period for administration of the activators can be from about ½ to about 3 hours but preferably all activators are administered in a one hour period. Preferably the amount of tissue type or prourokinase type plasminogen activators is one half or less than the amount that would be used if used alone. The weight ratio between streptokinase and the other plasminogen activator or activators used with it can vary greatly. Sterile infusion fluids are preferred as a method of administering the pharmaceutical compositions to the body. Dosages can be applied to the body by injection into body fluids such as veins, arteries or the like as well as by intramuscular use or intragastric ingestion or injection into other normal or pathological body fluids or cerebral spinal fluid, pleural exudates, pertoneal fluid or ascites. Infusion fluids can be sterile normal saline. Other common excipients comprising conventional or suitable medium can be used to form the pharmaceutical composition. (e.g. ringers solution, dextrose solutions and the like)

The dosage level used when administering the pharmaceutical composition to a human patient can be the same or lower than that required for each agent separately. It is preferred that the dosage level be lower for each because of the advantageous interaction of streptokinase in combination with other plasminogen activators. It is preferred that each dose would be less than 50% of the effective dose of each plasminogen activator or streptokinse when used separately. SK is used at a dose low enough to avoid a general fibrinolytic effect to the body and consequential hemorrhagic complications. The above dosage rates are particularly applicable to cases of myocardial infarction and are also useful for other thromboembolic disease such as deep vein thrombosis and pulmonary embolism. However, in some cases of such other thrombolytic disease the time period of administration or other values may vary.

In an example of using the method in composition of this invention a mixture of streptokinase and prourokinase of the type shown in FIG. 1 is formed by suspending 250,000 units of streptokinase and 30mg scu-PA in 500 ml of normal saline. This solution is used as an infusion fluid and injected into a human who has experienced a myocardial infarction. It is expected that advantageous clot lysis will occur.

In another group of examples, the thrombolytic effect of various agents in combination is carried out in Macaca arctoides monkeys. Each animal received 15 RPMI units of human plasminogen i.v. just before the experiment was intitiated.

| Monkey No. | Drug and dose schedule | Thrombolysis decrease in labeled clot radioactivity in 12 hours | Changes in peripheral blood coagulation factors |
|---|---|---|---|
| 1 | Saline i.v. 12 hr. | 12 | 0 |
| 2 | Saline i.v. 12 hr. | 14 | 0 |
| 6 | pro-UK 4000 u/kg i.v. 30 min. + 2000 u/Kg/hr, i.v. 11.5 hr. | 49 | 0 |
| 130 | t-PA 0.25 mg/kg i.v. 1 hr | 16 | 0 |
| 131 | t-PA 1.25 mg/kg i.v. 3 hr. | 56 | + |
| 134 | t-PA 0.25 mg/kg i.v. 1 hr + pro-UK 2000 u/kg, i.v. 11 hr | 79 | 0 |
| 132 | SK 2500 u/Kg, i.v. 1 hr. | 15 | 0 |
| 5J | SK 25,000 u/Kg, i.v. 30 min + 75,000 u/KG/hr, i.v. 6 hr. | 60 | + |
| 134 | SK 2500 u/Kg i.v. 1 hr. + pro-UK 2000 u/Kg/hr i.v. 11 hr. | 74 | 0 |

It is expected that a synergistic effect will be obtained by the use of streptokinase in conjunction with t-PA type and/or scu-PA type plasminogen activator. Larqer thrombolytic effects are obtained with the use of the streptokinase and another plasminogen activator then would be expected to be obtained with each individually.

What is claimed is:

1. A thrombolytically active pharmaceutical composition comprising a combination of streptokinase and a second plasminogen activator which is a prourokinase plasminogen activator.

2. A thrombolytically active pharmaceutical combination in accordance with claim 1 and comprising a mixture of streptokinase and said second plasminogen activator in normal saline.

3. A thrombolytically active pharmaceutical composition in accordance with claim 1 wherein said streptokinase is in an amount of from 1,000 to 25,000 international units/kilogram of body weight, and said second plasminogen activator is in an amount of from 0.1 to 1.0 mg per Kilogram of body weight.

4. A method of treating a body to obtain a thrombolytic effect in vivo, said method comprising applying streptokinase and a second plasminogen activator which is a prourokinase plasminogen activator so that said streptokinase and plasminogen activator co-act to obtain a desired therapeutic effect in the body.

5. A method in accordance with a method of claim 4 wherein said streptokinase and second plasminogen activator are applied to the body in sequence.

6. A method in accordance with a method of claim 4 wherein said streptokinase and second plasminogen activator are simultaneously applied to the body.

7. A method in accordance with a method of claim 4 wherein said streptokinase is applied to the body at a rate and dosage lower than causes a thrombolytic effect if used by itself and said second plasminogen activator is applied at a dosage lower than would cause a thrombolytic effect to the body if used by itself.

8. A method in accordance with a method of claim 4 wherein said streptokinase is used in an amount of 1,000 to 25,000 units/Kg. of body weight.

9. A method in accordance with a method of claim 8 wherein said second plasminogen activator is applied in an amount of from 0.05 to 1.0 mg/Kg. of body weight.

10. A method in accordance with claim 4 wherein said streptokinase is used in an amount of from 2,000 to 12,500 units/Kg. of body weight.

* * * * *